United States Patent [19]

Schnell et al.

[11] Patent Number: 4,900,389

[45] Date of Patent: Feb. 13, 1990

[54] METHOD OF SEALING AN ARTICLE VIA RADIO FREQUENCY

[75] Inventors: William J. Schnell; John M. Munsch, both of Libertyville; Robert W. Flagler, Barrington; Eugene Fabisiewicz, Mount Prospect, all of Ill.; Pierre Soubrier, Brussels, Belgium

[73] Assignee: Baxter Travenol Laboratories, Inc., Deerfield, Ill.

[21] Appl. No.: 231,647

[22] Filed: Aug. 9, 1988

Related U.S. Application Data

[63] Continuation of Ser. No. 918,169, Oct. 10, 1986, abandoned.

[51] Int. Cl.$^4$ .............................................. B32B 31/28
[52] U.S. Cl. .............................. 156/273.7; 156/274.4; 156/275.1; 156/294; 156/303.1; 156/308.7; 156/308.4; 156/309.6
[58] Field of Search ................ 156/73.1, 272.4, 273.7, 156/274.4, 275.1, 294, 303.1, 308.2, 308.4, 309.6, 380.2, 380.5; 604/408–410, 905, 262; 128/DIG. 24; 220/202, 75–76, 84 B; 428/36

[56] References Cited

U.S. PATENT DOCUMENTS

| | | |
|---|---|---|
| 2,816,596 | 8/1955 | Welch, Jr. |
| 3,222,590 | 3/1964 | Clark . |
| 3,558,397 | 2/1968 | Clark . |
| 3,706,620 | 12/1972 | Dykstra . |
| 4,417,753 | 11/1983 | Bacehowski et al. . |
| 4,419,095 | 12/1983 | Nebergall et al. . |
| 4,547,641 | 10/1985 | Nebergall et al. . |
| 4,576,671 | 3/1986 | Shimahaka . |

FOREIGN PATENT DOCUMENTS

| | | |
|---|---|---|
| 59-42920 | 3/1984 | Japan . |
| 59-42921 | 3/1984 | Japan . |
| 59-178214 | 10/1984 | Japan . |
| 60-4030 | 1/1985 | Japan . |

Primary Examiner—Merrell C. Cashion, Jr.
Attorney, Agent, or Firm—Charles R. Mattenson; Paul C. Flattery

[57] ABSTRACT

A method of radio frequency sealing attaches a seal member to a cylindrical, hollow, access port of a container. The method uses two sets of spaced apart die elements to generate an axial electric field along a region where the port and seal member overlap. An external peripheral ring is formed about an exterior surface of the port. The method can be used with containers having a sealed periphery as well as those previously filled with a fluid.

2 Claims, 3 Drawing Sheets

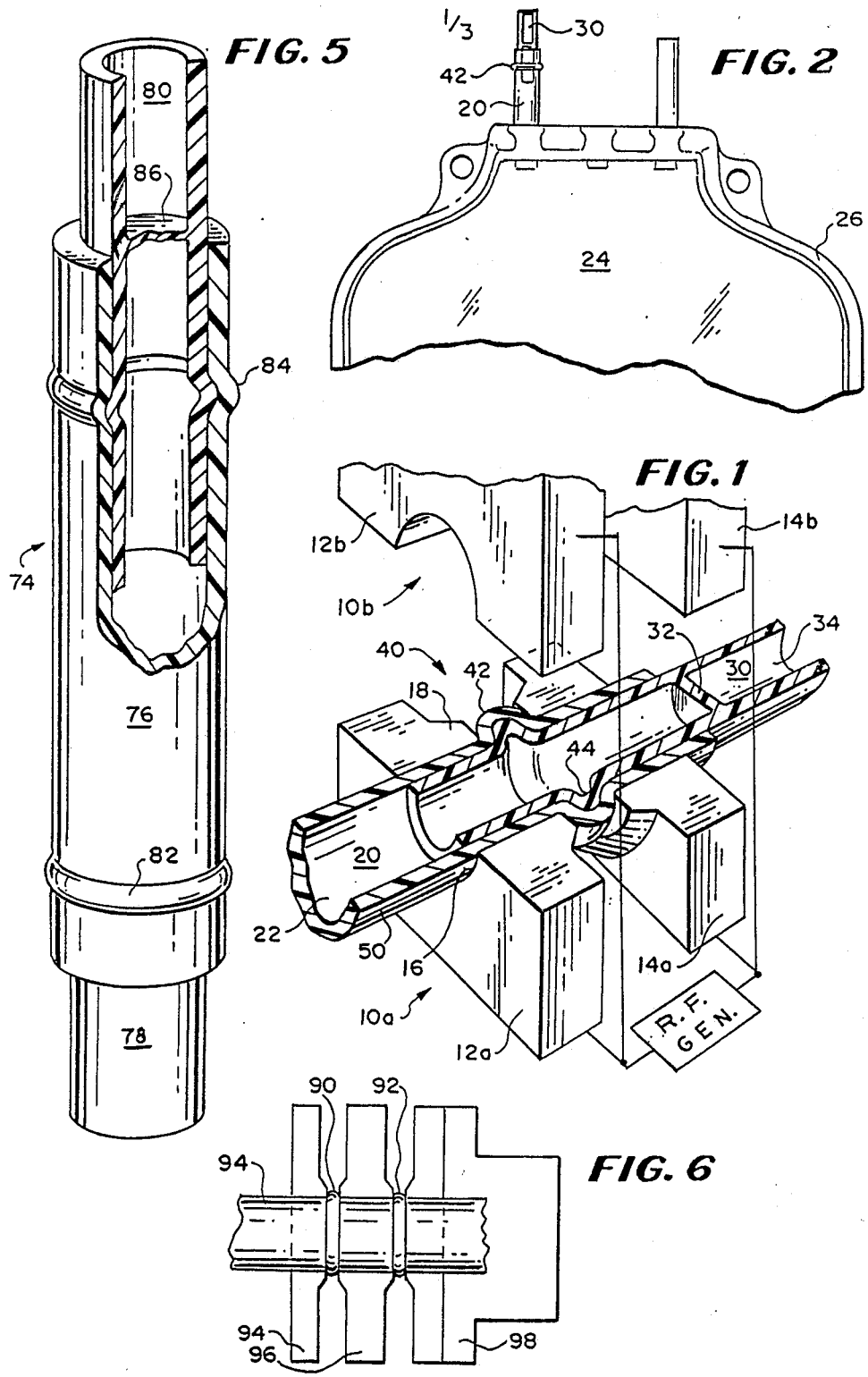

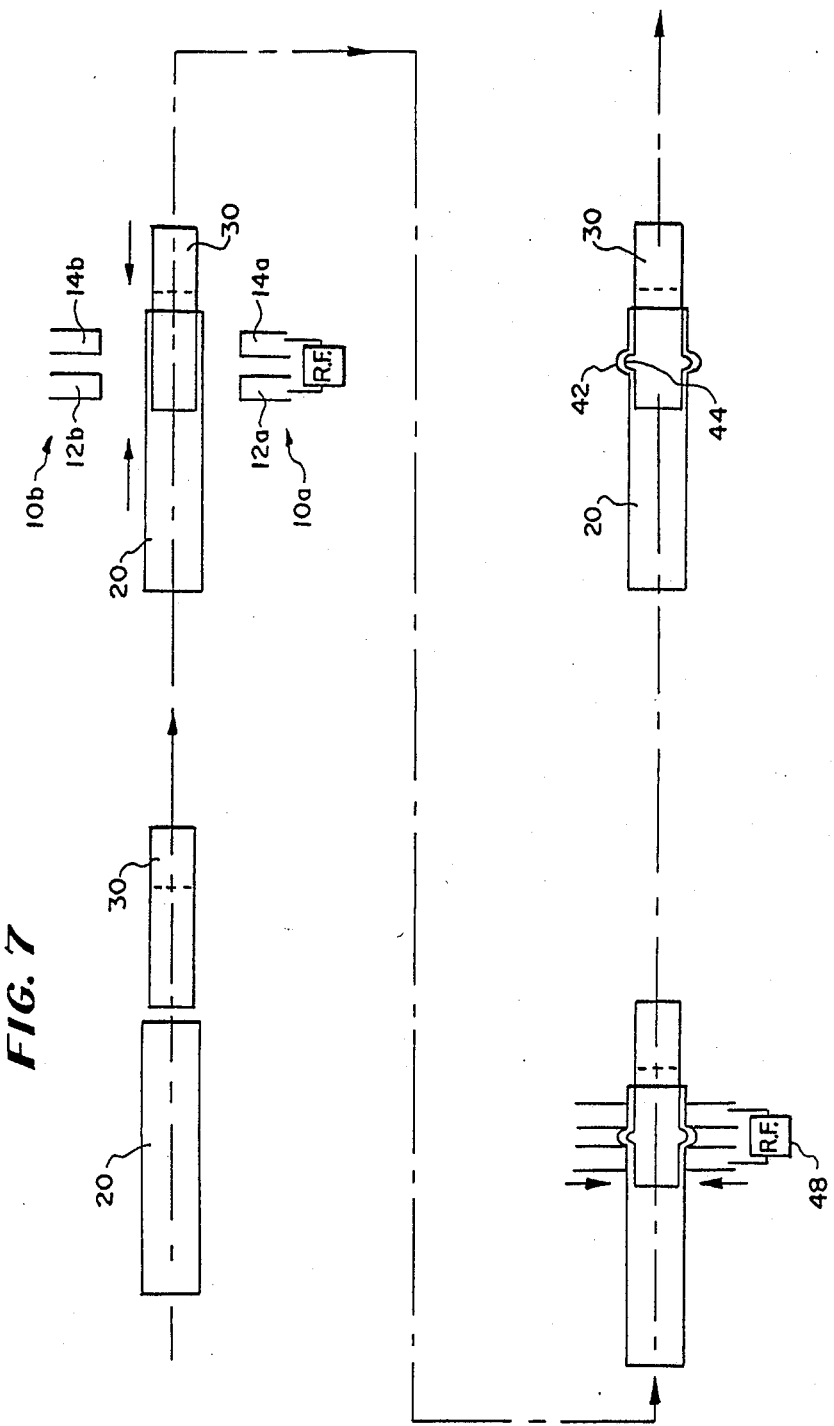

METHOD OF SEALING AN ARTICLE VIA RADIO FREQUENCY

This application is a continuation of application Ser. No. 918,169 filed Oct. 10, 1986, now abandoned.

FIELD OF THE INVENTION

The invention pertains to a method of affixing a seal member to an access port of a container. The invention also pertains to the article of manufacture that results from the method. More particularly, the invention pertains to an article and method of making same wherein a container has a pierceable, access seal member affixed thereto by means of radio-frequency heating.

BACKGROUND OF THE INVENTION

It is known from the prior art to provide fluids in sealed flexible, plastic containers. Such fluids are often medically related. Such containers usually contain an access port affixed thereto. This access port can be opened by means of a suitable connector in order to deliver the fluids within the container to a patient.

The seals used with such containers are often cylindrical with a pierceable, closing membrane affixed to an interior peripheral surface of the cylindrical member. The cylindrical member can be affixed to the access port of the container in a variety of ways.

One method known from the prior art is to use a plastic solvent which softens and melts an exterior, peripheral surface of the cylindrical seal member as well as an interior cylindrical surface of the port of the container. The seal member is inserted into the cylindrical port. Upon evaporation of the solvent, a fluid resistant bond is formed between the two members.

Alternately, the seal member can be inserted into the cylindrical port. An electrically, energizable mandrel can be inserted through an open seam or peripheral edge of the container and into the seal member. An external radio frequency electrode can be positioned outside of the container, adjacent the port. Supplying an electrical potential at a selected radio frequency between the inner mandrel and the outer electrode creates a heating electric field which extends radially through the port and through the cylindrical sealing member to the mandrel.

This radio frequency electrical field heats the material of the port as well as the cylindrical sealing member in the region of the electrode. The heated materials melt and fuse together thereby creating, on cooling, a liquid resistant bond between the seal member and the port of the container.

While the above two noted methods provide effective liquid resistant seals, there are times when it would be useful to be able to affix a sealing member to a port of a closed container without the use of a solvent. If the container is closed, there is no opening available to insert a mandrel therein as described above. Hence, there is a need for a radio frequency sealing method usable with containers having a closed peripheral boundary. These containers may or may not have been previously filled with a fluid.

SUMMARY OF THE INVENTION

In accordance with the invention, an article usable in the delivery of medical fluids is provided. The article includes a container which has a closed periphery and which is suitable for receiving a selected fluid. The container includes an access port. A seal member is slidably engageable with the access port of the closed container. The seal member is affixed to the access port by an annular region formed of melted and resolidified material from the seal member and from the port.

The port can have a generally cylindrical shape with an interior cylindrical surface. The region of solidified material in such an instance is annular in shape and surrounds an exterior peripheral surface of the port. An annular depression is defined on an interior peripheral surface of the seal member. This annular depression is offset from but coextensive with the annular exterior bead.

The container can have a generally rectangular shape of a conventional variety with an interior region for receiving the medical fluid. Alternately, the container could itself be a cylindrical member with a seal member affixed to each end thereof.

In order to provide a seal of especially high reliability, two or more spaced apart fused annular regions can be formed about the port member. In this embodiment, the seal member is affixed to the port member by multiple spaced apart annular sealing regions.

Further, in accordance with the invention, a method of radio frequency sealing a member to a container is provided. The method includes the steps of providing first and second sets of radio frequency dies. Each set of radio frequency dies contains first and second elements. The elements of the first die set are positioned adjacent but spaced apart from one another. The seal member is slidably engaged with an interior surface of the port. The port to be sealed is placed into contact with the spaced apart elements of the first die set. A region where the seal member is to be affixed to the port is located adjacent the space between the two spaced apart die elements.

The elements of the second die set are positioned adjacent to but spaced apart from one another. The second set of spaced apart die elements are moved into compression contact with the port. The location of the space between the elements of the first die set is adjacent to but laterally displaced from the location of the space between the elements of the second die set.

A selected electrical potential is applied between the two spaced apart elements of the first die set. The same electrical potential is applied between the two spaced apart elements of the second die set. An axially directed radio frequency electric heating field is thereby impressed on the port and the inserted sealing member. The radio frequency heating field heats and fuses an annular or ring-shaped region of the port between the spaced apart die elements to the seal member. On removal of the electric field, the heated and fused region cools and resolidifies. A liquid resistant seal that is annular or ring-shaped is thus formed between the port and the inserted seal member.

In accordance with the above-noted method, the electric field extends axially along the port of the container. An annular or ring-shaped bead is formed in the space between the two sets of spaced apart die elements, on the exterior surface of the port.

Numerous other advantages and features of the present invention will become readily apparent from the following detailed description of the invention and the embodiments thereof, from the claims and from the accompanying drawings in which the details of the invention are fully and completely disclosed as a part of this specification.

DESCRIPTION OF THE DRAWINGS

FIG. 1 is an enlarged, partially fragmentary view, of first and second open die sets with a combined port and seal member shown positioned in spaced apart die elements, partly in section;

FIG. 2 is a planar fragmentary view of an article in accordance with the present invention;

FIG. 5 is a view, partly broken away, illustrating an alternate article in accordance with the present invention;

FIG. 6 is a schematic view illustrating formation of an alternate seal member in accordance with the invention; and FIG. 7 is a flow diagram illustrating the steps of a method in accordance with the present invention.

DETAILED DESCRIPTION OF THE PREFERRED EMBODIMENTS

Figure 3:
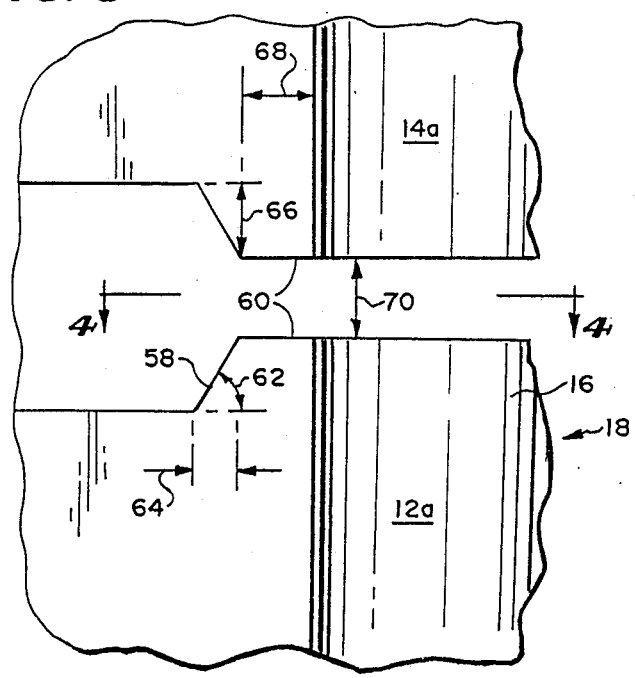
FIG. 3 is an enlarged, fragmentary, top planar view of spaced apart first and second die elements in accordance with the present invention.

While this invention is susceptible of embodiment in many different forms, there is shown in the drawing and will be described herein in detail specific embodiments thereof with the understanding that the present disclosure is to be considered as an exemplification of the principles of the invention and is not intended to limit the invention to the specific embodiment illustrated.

In accordance with the figures, FIG. 1 illustrates a set 10a of spaced apart die members or elements 12a and 14a. The die elements 12a and 14a each include a semicircular bore, such as the bore 16 formed therein and extending therethrough. A semi-circular flange 18 extends axially from each of the die elements. Each flange 18 is oriented toward and is adjacent to a corresponding flange on an adjacent die element.

Spaced laterally from the first die set 10a is a second die set 10b. The die set 10b includes first and second spaced apart die elements 12b and 14b. Die elements 12b and 14b are shaped corresponding to the elements 12a and 14a, respectively.

The spaced apart die elements 12a and 14a are designed to receive a cylindrical port 20. The port 20 has an interior peripheral surface 22. The port 20 might be affixed to a container 24. The container 24 could have a closed peripheral boundary 26.

It will be understood that the present method could be used in combination with containers whose peripheral boundaries have not previously been sealed. However, an important aspect of the present method lies in the fact that it can be used in conjunction with containers, such the container 24, which have a previously sealed periphery.

A seal member 30 of a generally cylindrical shape includes a sealing membrane 32 which is affixed to an interior peripheral surface 34 of the member 30. The member 30 slidably engages the interior peripheral surface 22 of the port 20. When so engaged, the membrane 32 is effective to close the port 20.

The seal member 30 is affixed to the port 20 in an annular region 40. The region 40 is located between the spaced apart die elements 12a and 14a and 12b and 14b.

The second set of spaced apart die elements 12b and 14b is moved into compression contact with the port 20. The two sets of die members 10a and 10b radially compress the port 20 and the seal member 30 in the axial spaces therebetween forming an outwardly extending annular region or ring 42. An interior annular depression 44 is formed in the seal member 30 positioned adjacent the annular exterior region 42.

In order to attach the seal member 30 to the port 20, a radio frequency generator 48 provides radio frequency signals to the spaced apart die elements 12a, 14a and 12b, 14b. The signals from the radio frequency generator 48 extend axially along the port 20 and seal member 30 melting and fusing together the material thereof in the region 40. This melting and fusing process connects the region 40 to an annular exterior bead or ring 42 of melted material on an exterior peripheral surface 50 of the port 20. In addition, the annular depression 44 is fixed on the interior surface 34 of the port 30. The annular depression 44 is adjacent to but offset from the exterior ring or annular region 42.

To facilitate the heating and fusing process, each of the die members 12a, 14a and 12b, 14b includes the axially extending flange 18. These flanges, such as the flange 18 are semicircular in shape. The radio frequency electric field is coupled between adjacent flange members.

Figure 4:
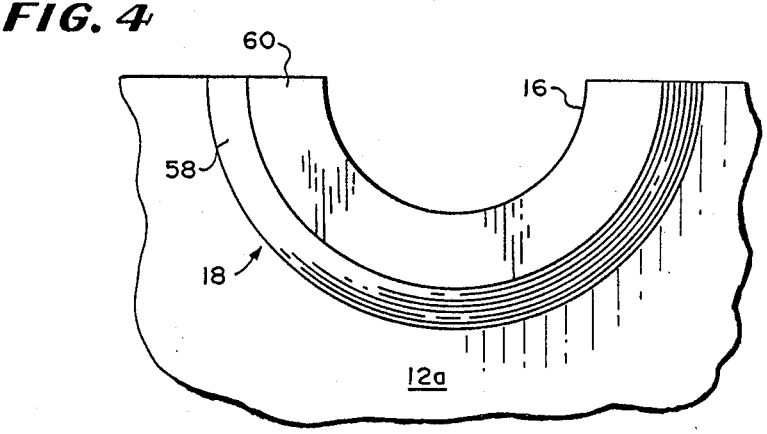
FIG. 4 is a view taken along line 4—4 of FIG. 3.

FIGS. 3 and 4 are fragmentary, enlarged views of the spaced apart die elements 12a and 14a illustrating the axially extending flanges such as the flange 18. The elements 12b and 14b have correspondingly shaped flanges. Each of the flanges has a tapered annular peripheral surface 58. Surface 58 terminates in a planar, semicircular front surface 60. Adequate sealing of the seal member 30 to the port 20 occurs when the annular surface 58 is at an angle 62 on the order of 53 degrees with respect to the die element 12a. Alternately, the angle 62 could be equal to 90 degrees. The base or largest radius of the annular surface 58 could be as large as three-quarters of an inch if desired.

In a particular embodiment of the die members, the dimension 60 was on the order of 0.030 inches, and the dimension 64 was on the order of 0.030 inches. The dimension 66 was on the order of 0.040 inches. The dimension 68 was on the order of 0.030 inches. The spacing between the die members, such as 12a and 14a was in a range of 1/16-⅛ inches.

An exemplary RF generator 48 found to generate an appropriate radio frequency field was a Callanan Model Number 20, 2 kw generator. The following settings gave desired fusing in the region 40 with a PVC port 20 and a PVC seal member 30:

GRID #2
Heat 80
Time 2 seconds
Variac set at 100%.

The assembled port 20 and seal member 30 have a diameter in a range of 0.320 inches to 0.325 inches. When die elements 12a and 12b are brought together, the semicircular bores 16, now form a cylindrical opening through the die elements 20 and 30. This cylindrical bore or opening has a diameter in a range of 0.278 inches to 0.281 inches.

FIG. 5 illustrates an alternate form of an article 74 in accordance with the present invention. The article 74 include a tubular hollow body portion 76 which is closed by seal members 78 and 80. In accordance with the present method, seal member 78 can be slidably inserted into the body member 76 and a ring seal 82 of the type described above can be formed therebetween. The container 76 can then be filled with a selected fluid. The second seal member 80 can be slidably inserted therein and a second seal 84 formed therebetween. This results in a sealed container 76 filled with fluid. The contents of the container 76 can be accessed by piercing a membrane 86.

In a further embodiment of the present invention, as illustrated in FIG. 6, multiple spaced apart ring seals 90 and 92 can be formed in a member 93. The multiple seals 90, 92 provide additional security. The seals 90, 92 can be formed by a plurality of spaced apart die elements such as 94 through 98. As in the case of FIG. 1, the die elements 94 through 98 would have a corresponding set of laterally displaced die elements which would be brought into contact with the container or port 93 onto which the seals 90, 92 are to be formed. These die elements also include flanges such as the flange 18.

FIG. 7 illustrates in further detail the steps of the method of sealing the port 20 to the seal member 30. The seal member 30 is slidably engaged with the port member 20. The region wherein the seal member 30 and port member 20 overlap is placed between the first and second elements of die sets 10a and 10b. The die sets 10a and 10b are then brought into compression contact with the overlapping region of the seal member 30 and the port 20 therebetween. The radio frequency generator 48 is then energized and an axial electric field is created between the die members 12a, 14a and between the die members 12b and 14b. This field heats and melts part of the overlapping region of the seal member 30 and the port member 20 between the respective die elements. The annular bead 42 is formed on the exterior peripheral surface of the port member 20. The interior annular depression 44 is fixed on the interior peripheral wall 34 of the seal member 30.

While a flexible rectangular shaped container 24 and a tubular container 76 have been illustrated herein, it will be understood that the exact shape of the container is not a limitation of the present invention. Similarly, it will be understood that the precise exemplary setting provided above with respect to the RF generator 48 is also not a limitation of the present invention. The dimensions of the die elements, including the dimensions of the flanges 18 can also vary without departing from the spirit and scope of the present invention.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A method of radio frequency sealing the bore of a port with a previously sealed member without the use of an electrode or mandrel within said bore, said method comprising the steps of assembling said sealed member to an end portion of the port forming a junction therebetween having an axial bore, locating at least a portion of the junction between external first and second sets of radio frequency dies, each set having first and second die elements, the first die elements of the sets being generally oppositely radially spaced relative to axis of the junction bore, the second die elements of the sets being each generally equally spaced from the associated first die element axially along the axis of the junction bore with the region of the junction intended to be sealed lying in the axial space defined between the first and second die elements, moving the first and second external die sets into compression contact with the junction to radially compress the region of the junction lying within the axial space without compressing the bore of the junction closed, thereby forming an outwardly extending annular ring on the exterior of the junction and between the respective first and second dies of each set, and a corresponding outwardly extending annular depression on the interior of the junction bore, and sealing the sealed member to the end portion of the port by applying a selected energy potential between the elements of the external die sets, without the use of an electrically energizable mandrel in the bore of the junction, to create a heating field that melts and fuses the junction in the region of the annular exterior ring and annular interior depression.

2. A method according to claim 1 wherein, in said step of sealing the sealed member to the end portion of the port, the electric potential is applied to direct the heating field axially along the junction bore.

* * * * *